United States Patent

Duan et al.

[11] Patent Number: 5,962,029
[45] Date of Patent: Oct. 5, 1999

[54] IODINE GERMICIDES THAT CONTINUOUSLY GENERATE FREE MOLECULAR IODINE

[75] Inventors: Yongjun Duan, Lexington; Jack Howard Kessler, Southborough, both of Mass.

[73] Assignee: Symbollon Corporation, Framingham, Mass.

[21] Appl. No.: 08/677,367

[22] Filed: Jul. 5, 1996

[51] Int. Cl.⁶ .......................... A61K 33/18; A01N 59/12
[52] U.S. Cl. .......................... 424/613; 424/669; 424/670
[58] Field of Search .................................. 424/78.3, 669, 424/670, 613

[56] References Cited

U.S. PATENT DOCUMENTS

| | | | |
|---|---|---|---|
| 3,215,627 | 11/1965 | Tools | 210/62 |
| 3,232,869 | 2/1966 | Gard | 210/62 |
| 4,401,434 | 8/1983 | Harris | 428/78.25 |
| 4,822,512 | 4/1989 | Auchincloss | 252/106 |
| 4,989,733 | 2/1991 | Patry | 252/106 |
| 5,314,968 | 5/1994 | Frommer et al. | 525/356 |
| 5,389,384 | 2/1995 | Jooste | 424/661 |
| 5,405,526 | 4/1995 | Sutera | 210/124 |
| 5,409,697 | 4/1995 | Gluck | 424/78.25 |

*Primary Examiner*—Peter F. Kulkosky
*Attorney, Agent, or Firm*—E. Lieberstein

[57] ABSTRACT

A method for forming an iodine disinfecting solution that continuously generates free molecular iodine at a controlled average rate of at least 0.2 ppm per hour over a sustained and extended time period. The method involves combining persulfate anions and iodide anions in sufficient quantity in an aqueous medium having a resulting pH of less than about 6.5 so as to create an iodine generating capacity in said aqueous medium of between 1.5 and 6.5 with a generated concentration of at least 5 ppm of free molecular iodine and maintaining this concentration over the course of the extended time period.

15 Claims, No Drawings

IODINE GERMICIDES THAT CONTINUOUSLY GENERATE FREE MOLECULAR IODINE

FIELD OF THE INVENTION

This invention generally relates to iodine disinfectants and sterilants, and in particular, to iodine germicides that continuously generate free molecular iodine.

BACKGROUND

Many examples of commercial iodine products containing 0.5 to 20% iodine by weight are known. There are presently only one or two examples of iodine products that contain 0.1% iodine or less. One reason for this is that almost all commercial iodine products are concentrates. These iodine concentrates ordinarily call for dilution with water prior to use. The dilution is usually in the range of 1:100 to 1:1000. The diluted product is discarded after use, since the iodine content of the solution continuously decreases over the course of several hours and the germicidal activity of the solution quickly decreases below acceptable levels.

There are also iodine products that are not diluted prior to use, such as hand-washing compositions, bovine teat dip products, and products for human topical disinfection. The level of total iodine contained in all of these products is much higher than the minimum iodine concentration required for biocidal efficacy. Despite the fact that these products do not require high iodine levels for effectiveness, it is necessary to include elevated iodine levels in order to achieve adequate product stability. However, one drawback of such compositions is that the inclusion of elevated iodine levels contributes to undesirable toxicological properties and unwanted interactions with inanimate materials.

The prior art contains examples of instantly generating iodine in order to provide a germicidal activity. U.S. Pat. No. 3,232,869 teaches a method for purifying and disinfecting aqueous liquids with free molecular iodine, where the iodine is provided by quantitatively oxidizing iodide ion into free molecular iodine with persulfates in the pH range between 7 and 8. This patent requires the use of a stoichiometric amount of either iodide or persulfate to yield a free iodine concentration of 0.1 to 1.0 ppm of free molecular iodine.

U.S. Pat. No. 3,215,627 discloses a method for use in the disinfection of swimming pools. A pH range of 7 to 8 is taught as critical to both U.S. Pat. Nos. 3,232,869 and 3,215,627. The range of free molecular iodine that is generated according to the method of the '627 patent is between 0.2 and 0.4 ppm. This patent also teaches that an iodide bank is of no value because iodine release is erratic and unpredictable and because it is not possible to achieve or maintain a desired iodine level.

U.S. Pat. Nos. 3,215,627 and No.3,232,869 identify a concentration range of 0.1 to 1.0 ppm of iodide ion as the practical concentration range. This concentration of iodide equates to a theoretical maximum free molecular iodine concentration of 0.85 ppm. Moreover, both the '627 and '869 patents teach that a pH in the range of 7 to 8 is critical.

SUMMARY OF THE INVENTION

In one aspect, the invention features a method of preparing an iodine-containing disinfecting solution. The method comprises the steps of providing a persulfate salt; providing an iodide salt; and combing the persulfate salt and the iodide salt in an aqueous medium having a pH less than or equal to about 6.5 to generate free molecular iodine at a rate of at least 0.2 ppm per hour for an extended period of time.

In another aspect, the invention provides a disinfecting composition for generating free molecular iodine. The composition comprises a persulfate salt; an iodide salt; and an aqueous medium having a pH less than or equal to about 6.5; the composition being effective, upon combining the persulfate salt and the iodide salt, in the aqueous medium, to generate free molecular iodine for an extended period of time at a rate that is at least 0.2 ppm such that iodine is maintained at a desired concentration. The composition can be packaged such that the iodide salt and the persulfate salt are isolated from each other within the same container. The contents of the container can be added together in an aqueous medium, at a pH less than or equal to about 6.5, to initiate the iodine-generating reaction.

DETAILED DESCRIPTION OF THE INVENTION

For convenience, certain terms employed in the specification, examples, and appended claims are defined below.

The term "thiosulfate titrable iodine" or "total iodine" is a term of art, and, as used herein, refers to iodine species which can be titrated by thiosulfate. Total iodine includes free molecular iodine and triiodide, since they are both titrated by sodium thiosulfate.

The term "rate of iodine generation" as used herein, refers to the rate at which free molecular iodine formed from the oxidation of iodide anion by the peroxydisulfate anion. The rate of iodine generation is a critical feature of this invention since different applications contemplated under this disclosure, e.g., instrument disinfectant, disinfection of dental water lines, disinfection of hemodiazlyzers, hard surface disinfectant, teat sanitizer, etc.., require different rates of iodine generation.

The term "slow oxidant" or "slow oxidizer," as used herein, refers to an agent that can oxidize iodide anion to molecular iodine over an extended period of time, in contrast to "fast" oxidants which rapidly and quantitatively oxidize iodide to iodine. For example, the oxidation of iodide by a slow oxidant such as persulfate can be made to occur over a period of hours or days.

The term "source of persulfate anion" or "persulfate salt," as used herein, means any material alone or in combination which can serve as a precursor for persulfate anion. Persulfates are also known as "peroxydisulfates." Sources of persulfate anion include sodium persulfate, ammonium persulfate and potassium persulfate.

The term "iodine species ratio," as used herein, refers to the ratio of free molecular iodine ($I_2$) to other iodine species such as iodide and triiodide.

The term "iodine generation capacity," as used herein, refers to the quantitative ability of a composition of matter to generate free molecular iodine over its proscribed use-life for those compositions which require an initial level of free molecular iodine before they are useful. For example, the iodine generation capacity for a composition which initially contains only free molecular iodine, and no other iodine species, is 0; that is, this composition does not have the ability to replace the initial concentration of free molecular iodine once it is consumed from the system. An iodine generation capacity of 1 indicates that a composition has the ability to replace up to a maximum of one time all of the initial free molecular iodine. Similarly, an iodine generation capacity of 10 means that a composition has the ability to replace up to a maximum of ten time all of the initial free molecular iodine that is consumed.

The iodine generation capacity referred to in this application does not rely upon a large reserve of triiodide to serve as a source of potential free molecular iodine. In contrast to traditional iodophores, compositions based upon the present invention rely upon the continuous generation of free molecular iodine at a predetermined rate. By avoiding the use of triiodide the compositions of matter contemplated under this invention expect to obviate many of negative features e.g., staining, irritation, of traditional iodine compositions.

The term "iodide salt" refers to any salt of the iodide anion which yields the iodide anion when dissolved in an aqueous medium. Suitable counter-ions for the iodide anion include sodium, potassium, calcium, and the like, as well as ammonium cations.

A "source of initial free molecular iodine" or "initial iodine source," as used herein, refers to a source of iodine that rapidly generates a selected concentration of molecular iodine. For example, molecular iodine, when added to a composition, immediately generates a selected concentration of free molecular iodine in solution. Other sources of initial iodine include iodophores and combinations of iodide anion with a fast oxidant.

Below a pH of 7.0, iodine atoms assume three principal forms. These three forms are triiodide, iodide and free molecular iodine; of these three species, only free molecular iodine is biocidal. At a pH of 7.0 and above hypoiodous acid is formed in substantial concentrations. Hypoiodous acid is biocidal but its biocidal activity is substantially less than free molecular iodine on a molar basis.

Free molecular iodine is lost from an aqueous medium in several ways. Free molecular iodine is hydrated by water and, in an aqueous system, undergoes hydrolysis through a complicated series of reactions that can be summarized in the following two equations:

  (1)

  (2)

The hydrolysis products—iodate ($IO_3^{31}$) and iodide ($I^-$)—have no significant antibacterial activity. Elevated or basic pH values speed up iodine hydrolysis by consuming the protons formed by hydrolysis of elemental iodine. The relative rates of hydrolysis of free molecular iodine were measured at different pH values and the data are set forth in Example 1, infra. The data indicate that when the pH of a solution is equal to or greater than 7, iodine is hydrolyzed very rapidly. In contrast, iodine is hydrolyzed slowly when the pH is 6 or lower.

Free molecular iodine also evaporates considerably more rapidly than either iodide or triiodide, and, in the absence of organic matter and reducing agents, evaporation constitutes a major source of overall iodine loss in aqueous systems that freely exchange with the environrnent. Finally, free molecular iodine reacts with organic matter and is consumed as a result of this reaction.

Therefore, in order to maintain a defined minimum concentration of free molecular iodine, it is necessary for an effective iodine-containing germicidal solution to continuously generate or regenerate the free molecular iodine that is lost through the pathways described above. The subject invention is based, at least in part, on the observation that persulfates slowly oxidize iodide anions into free molecular iodine in an aqueous medium under the appropriate conditions; the rate of this oxidation reaction can be controlled and is reproducible. The continuous slow oxidation of iodide to iodine provides a source of biocidal iodine which effectively maintains germicidal activity over an extended period of time without requiring large reserves of triiodide such as those commonly found in iodophores.

Accordingly, in one aspect, the invention provides a disinfecting composition for generating free molecular iodine. The composition comprises a persulfate salt; an iodide salt; and an aqueous medium having a pH less than or equal to about 6.5. The composition is effective, upon combining the persulfate salt and the iodide salt, in the aqueous medium, to generate free molecular iodine for an extended period of time. In certain embodiments, the composition further includes an initial source of iodine. Preferably, when an initial concentration of free molecular iodine is required, the concentration of the initial free molecular iodine is at least about 5 ppm although 10 ppm may be preferred for certain applications.

The iodine compositions contemplated under this invention have an iodine generation capacity between 1.5 and 36. The iodine generation capacity and the rate of iodine generation provide some indication as to the minimum and maximum concentration of iodine that could be generated. It can be readily appreciated that the most suitable rate of iodine generation and iodine generation capacity will depend upon both the specific application and the local environment wherein the specific application is performed. For instance, one liter of a disinfectant that is contained in an unsealed glass jar that has a surface to volume ratio of 1000 will allow for more evaporation of free molecular iodine than would be observed with one liter of the identical disinfectant in a sealed glass container that had a surface to volume ratio of 100. Therefore it is impossible to preselect the most suitable ratio of iodide/persulfate unless one knows exactly how the composition will be used and the exact conditions of use.

In one embodiment the iodide salt and the persulfate salt may be provided in the same package as long as they are isolated from one another and maintained in a non-reactive condition. Various additives, including buffers, surfactants, detergents, dyes, perfumes, humectants, emollients, iodine sequestrants, anti-foaming agents, and anti-corrosive agents, may also be included within the pre-packaged container. Optionally, an initial source of free molecular iodine can be in the form of either free molecular iodine, triiodide another iodine precursor. An initial free molecular iodine source is sometimes useful where immediate iodine-derived germicidal activity is desired since it normally requires more than 5 minutes at room temperature for the reaction between the iodide and persulfate salts to generate germicidal-levels of free molecular iodine.

The formulations contemplated under this invention can be incorporated into a kit to facilitate use. The iodide and persulfate components of the kit should be packaged so as to preclude any oxidation of the iodide anion prior to the products intended use. The kit would preferably be configured so that the end-user could easily combine the contents of the kit into an aqueous medium for activation. The contents of the package should be able to be conveniently transported and/or stored until ready for use. To initiate the iodine-generating reaction, the contents of the package are emptied into an aqueous medium having a pH of less than or equal to 6.5.

The iodine-containing disinfectants of the invention provide several advantages. The subject disinfectant solutions utilize minimal concentrations of free and/or total iodine to achieve a desired efficacy, thereby minimizing the potential for unwanted toxicological reactions and objectionable reactions with inanimate materials. Another advantage is that the subject solutions can be reused without adding additional components and without the loss of germicidal activity.

Compositions

The present invention contemplates iodine compositions that: (1) contain between 5 and 10,000 ppm of thiosulfate titrable iodine, (2) have between 5 and 325 ppm free molecular iodine; (3) increase or substantially maintain the ratio of free molecular iodine to total iodine over a period of time, even under conditions that cause the loss of iodine atoms, and (4) have an iodine generation capacity between 1.5 and 36.

In general, germicidal compositions according to the invention will include iodide anion at concentrations between 50 and 10,000 ppm and most preferably between 100 and 500 ppm. The source of iodide anion can be any iodide salt which yields the iodide anion when dissolved in an aqueous medium. Examples of such salts include the sodium, potassium, calcium and ammonium salts, and mixtures thereof. The most preferred iodide salts include sodium iodide and potassium iodide. The iodide salt can be dissolved all at one time, or it can be dissolved gradually over time, as when a slow-release formulation is used. Iodide anion can be provided to the system in a liquid form if it is kept stable prior to use. Specifically, it is preferred that no contact occur between the iodide anion and the peroxydisulfate anion prior to dissolution in an aqueous environment.

The concentration of iodide that will yield a suitable level of iodine varies with the pH of the contemplated formulation. However, the useful range is between 0.05 and 10.0 grams per liter in the final reconstituted formulation. The preferred range for iodide anions is between 0.1 and 4.0 grams per liter in the final reconstituted formulation. Such concentrations of iodide anion, in combination with an appropriate amount of persulfate salt and at a suitable pH, are anticipated to yield a concentration of free molecular iodine in the range of 5 to 325 ppm, and more preferably a free molecular iodine concentration in the range of 10 to 150 ppm.

Germicidal compositions of the invention also include a slow oxidant, e.g., an oxidant which is capable of slowly oxidizing iodide anion to molecular iodine in a controlled and predictable fashion. A preferred slow oxidant is persulfate, e.g., a persulfate salt. As described in more detail below, the slow oxidant should be capable of oxidizing iodide to iodine over a period of hours or days. The persulfate salt can be any material which yields persulfate anion upon dissolution in an aqueous medium. Preferred persulfate salts include sodium persulfate, ammonium persulfate, potassium persulfate, and mixtures thereof. A combination of reactants which generate persulfate anion in situ can also be employed, provided that the reaction conditions are such that iodide is slowly oxidized to iodine.

The preferred concentration range for persulfate anion in the final composition is between 0.01 and 1% (w/w) in the final composition, more preferably between 0.04 and 0.2% (w/w) in the final composition. As with the iodide salts, persulfate salts can be dissolved all at one time, or can be dissolved gradually over time, as when a slow-release formulation is used. In several preferred embodiments, the persulfate salt is present in sub-stoichiometric quantities compared to the iodide salt, i.e., it is present in sub-molar quantities.

The stoichiometric ratio of iodide anion to persulfate anion is generally between 2:1 and 0.2:1. In certain preferred embodiments, the ratio of iodide anion to persulfate anion is at least 1:1. Thus, in preferred embodiments, an iodide "bank" or reserve can be maintained, such that excess iodide ion is present. In other preferred embodiments, the ratio of iodide anion to persulfate anion is less than about 1:1, more preferably about 0.7:1.

Buffering agents may be utilized to maintain pH within the desired range of 1.0 and 6.5, or within the more preferred range of 3.5 and 5.5. Suitable buffering agents for inclusion in the compositions of the invention include glycine-glycine-HCl, potassium hydrogen phthalate-phthalic acid, citric acid-$Na_2HPO_4$, citric acid-$KH_2PO_4$-$H_3BO_3$-diethylbarbituric acid-NaOH, citric acid-sodium citrate, dimethylglutaric acid-sodium dimethylglutarate, acetic acid-sodium acetate, succinic acid-sodium succinate, potassium hydrogen phthalate-dipotassium phthalate, sodium cacodylate-cacodylic acid, sodium hydrogen maleate-disodium maleate, $Na_2HPO_4$-$NaH_2PO_4$, sodium bicarbonate-5% $CO_2$, imidazole-imidazole HCl, boric acid-sodium borate, and the following buffers known to one skilled in the art: Tris, MES, BIS-TRIS, ADA, ACES and PIPES. Enough buffer is added to maintain the pH below 6.5 or, if preferred, within a defined pH limit that is less than pH 6.5. In general, a buffer concentration of at least 5 millimolar is utilized.

Aqueous mediums suitable for use in the present invention include water, mixtures of water and alcohols (such as methanol, ethanol, and isopropanol), or mixtures of water and other water-miscible solvents. In general, an aqueous medium will be capable of dissolving iodide salts and persulfate salts, and will not react rapidly with free molecular iodine. In preferred embodiments, the aqueous medium is substantially non-toxic. In preferred embodiments, the aqueous medium is at least 50% water by volume.

Compositions contemplated by the invention can also include surfactants and/or detergents. Suitable detergents and surfactants include anionic, cationic, zwitterionic, non-ionic and ampholytic agents. These molecules are frequently used in formulations used for cleaning inanimate and animate surfaces. Representative compounds include sodium lauryl sulfate, lithium lauryl sulfate, alkyl benzenesulfonates, alkane sulfonates, alkene sulfonates, sulfated anionic detergents, sulfated anionic detergents, sulfonated anionic detergents, phosphated anionic detergents, carboxylated anionic detergents, Tween 20-polyoxyethylene sorbitan monolaurate, Tween 100, alkyl sulphates, alkyl ether sulphates, fatty acid amides, myristic acid, lauric acid, capric acid, caprylic acid, coconut and palm kernel fatty acids, N-acyl-sarcosinates, sodium-N-acyl-N-methyl taurates, sodium cocoylisothioate and amidopropyl betaines. The selection and concentration of these diverse surface active agents depends upon the application as one skilled in the art appreciates.

Some of the organic detergents listed above also have the ability to bind iodine and can thus potentially serve as sequestrants. For example, certain polyoxyethylene ethers that are commonly called Tritons can act as iodine sequestrants. The use of a detergent or surfactant that can also function as a sequestrant is contemplated in certain embodiments of the invention.

Other additives which may be employed in the compositions of the invention include dyes, perfumes, humectants, emollients, iodine sequestrants, anti-foaming agents, and anti-corrosive agents.

Representative humectants and emollients suitable for inclusion in the compositions contemplated in this application include sorbitol, dulcitol, glycerol, propylene glycol, acetamidopropyl trimonium chloride, lactamidopropyl trimonium chloride, acetamide MEA, lactamide MEA, lanolin, ethoxylated lanolins, polyethylene glycol-lanolin derivatives that contain lanolin dispersed onto polyethylene glycol, sorbitan isostearate, cetearyl octanoate, maleated soybean oil, cetyl lactate, lauryl lactate, dioctyl malate, myristyl lactate, tridecyl neopentanoate, glyceryl dilaurate, condensation products of primary and secondary alcohols, block polymers of ethylene oxide and propylene oxide and polyethylene glycol and polyethylene glycol derivatives.

Iodine sequestrants or complexing agents are well known in the art and examples can be found in various patents, including U.S. Pat. Nos. 2,931,777; 2,759,869; and 3,028,300. Examples of iodine complexing agents include non-ionic poly(ethylene oxide) homopolymers such as POLYOX N-10 and POLYOX N-12K, where POLYOX is a trade name of Union Carbide; block copolymers of ethylene oxide and propylene oxide such as PLURONIC F-38, PLURONIC F68, PLURONIC F 87 PRILL, PLURONIC F108 PRILL, PLURONIC 25 R4, PLURONIC P-105 where PLURONIC is a trade name of BASF Wyandotte; tetra-functional block copolymers derived from the sequential addition of propylene oxide and ethylene oxide to ethylenediamine such as TETRONIC 304 and TETRONIC 908 PRILL where TETRONIC is a trade name of BASF Wyandotte; polymers comprised of N, N-dimethyl-1-hexadeanamine oxide dihydrate such as ADMOX 14-85, ADMOX SC-1685 and ADMOX 18-85 where ADMOX is a trade name of Ethyl Corporation; polyvinylpyrrolidone; alkylphenol ethoxylates such as octyl-, nonyl- or dinonyl- phenoxypolyethoxy ethanol, and polymers comprised of ethoxylated alcohols that range from 8 to 18 carbon atoms in length such as NEODOL(R) 1-9 and NEODOL (R) 25-9 where NEODOL is a trade name of Shell Chemical Corporation. One skilled in the art will be able to identify other types of surfactants that can bind iodine.

In another practice of the invention, a slow oxidant (e g., a persulfate salt) can be added to a commercially available iodine germicide. The resulting composition can continuously generate iodine over an extended time. For example, addition of a persulfate salt to an iodine germicide such as WESCODYNE results in an iodine germicide that continuously generates free molecular iodine, as described in Example 6, infra. In this embodiment, the commercially available iodine germicide (e.g., Wescodyne) provides an initial source of free molecular iodine and can also provide or contribute to an iodide bank.

The compositions of the invention continuously generate free molecular iodine via the slow oxidation of iodide anion by persulfate anion. The concentration range of free molecular iodine contemplated in the invention is about 5 to about 325 ppm with a preferred range of about 10 to about 150 ppm. A minimum concentration of 10 ppm can be preferred because this level of free molecular iodine can be shown to have a significant and rapid effect on highly concentrated suspensions of bacteria (see Example 7). In some embodiments, a higher concentration of iodine is desirable. For example, the disinfection of endoscopes generally requires iodine concentrations of about 30 to 50 ppm to provide a margin of safety during use. In general, the concentration of free molecular iodine can be adjusted by adjusting the concentration of persulfate anion or iodide anion. Thus, increased concentrations of persulfate salt (and/or iodide anion) are expected to result in higher concentrations of free molecular iodine.

The rate of generation of free molecular iodine is mainly determined by the concentration of iodide anion and persulfate anion. It is critical to the practice of this invention to be able to control the rate of iodine generation since different applications will function optimally at different rates. It is possible to increase the rate of iodine generation by increasing either the iodide concentration or the persulfate concentration. At a constant concentration of iodide the rate of iodine generation will be increased by increasing the concentration of persulfate. At a constant concentration of persulfate the rate of iodine concentration will be increased by increasing the concentration of iodide.

The duration during which free molecular iodine is generated is determined by the concentration of iodide anion, the pH, the temperature and the concentration of persulfate anion. The invention contemplates compositions that continuously generate free molecular iodine for a minimum of 1 hour and a maximum of 20 days without requiring the addition of fresh reagents or time released chemicals. It is obvious to one skilled in the art that it would be possible to increase the time period over for generation of iodine by incorporating either iodide or persulfate into a time-release format.

The compositions of the invention gradually produce free molecular iodine in a controlled fashion over time, and, in the absence of initial added iodine, have low concentrations of free molecular iodine when initially constituted. In certain embodiments, it may be desirable to include additives which provide a suitable initial concentration of free molecular iodine. For example, iodine can be added to provide free molecular iodine; the concentration of free molecular iodine will subsequently be maintained by the oxidation of iodide to iodine. In another illustrative embodiment, a peroxidase and a source of peroxide can be used to rapidly generate initial iodine, as described in Example 8. In yet another embodiment, a small amount of persulfate can be activated by a promoter, e.g., a metal. For example, addition of a small amount (e.g., 5 mole %) of copper can activate a small amount of persulfate (e.g., 5 mole %). The "activated" persulfate rapidly oxidizes iodide anion to molecular iodine; the copper and "activated" persulfate are consumed. The slow oxidation of iodide by persulfate then continuously generates free molecular iodine over an extended period.

The term "regenerability" is employed in this application to express the rate at which free molecular iodine is generated and the duration of time over which free molecular iodine is generated. Different regenerabilities are required in different applications to offset the iodine loss that occurs during an application. For example, a high regenerability has to be provided in a case where iodine evaporates very quickly and a long application time is required. Many factors have an effect on the regenerability of a composition including the concentration of iodide and persulfate ions, pH value, temperature and additives. Therefore, routine experimentation may be necessary to find to a suitable regenerability for a specific application. Once a suitable regenerability has been identified for an application the iodide or persulfate concentrations can be adjusted to meet the requirements, as will be apparent to the skilled artisan.

For example, disinfection of endoscopes in a 10 minute time period generally requires a concentration of free molecular iodine of at least 20 and it is preferred to limit the concentration to less than 75 ppm compared to the disinfection of skin, which can require up to 150 ppm of free molecular. Thus, the concentrations of iodide anion and persulfate salt in a composition of the invention are preferably selected to result in a free molecular iodine concentration suitable for use in a particular application.

One advantage of the germicidal compositions of the invention is that the compositions retain germicidal activity over an extended period of time, e.g., for as long as two weeks. Thus, the germicidal compositions of the invention can be used repeatedly, rather than being discarded after a single use or a short period of use, as is the case with many prior art germicides. Accordingly, the present invention provides compositions which are economical and time-saving.

It should be noted that it is not essential to the successful practice of this invention that the iodine level in a reconstituted formulation remain the same during the time that it is intended for use. Rather, it is important that any change in iodine concentration be within the limits of variation that will not affect a desired performance level for the particular type product. Microbicidal iodine compositions of the present invention preferably have a pH equal to or less than 6.5. The more preferred pH range is between 3.5 and 5.5.

Products contemplated under this application will generally be stored or packaged in an unreacted state prior to use. An unreacted state is one in which conditions exist which prevent iodide oxidation by persulfate ion or other oxidants.

The compositions of the invention can be reconstituted in an aqueous environment some period of time prior to their intended use and an initial reaction then generates a defined level of free molecular iodine. One method of packaging is to compartmentalize a salt of persulfate in one chamber of a package and to include iodide anions in another, separate chamber of the package. Additional components can be placed in separate compartments if they prove to be incompatible. It is possible to include liquid components within the package provided that the liquid components are maintained in a state that precludes the oxidation of iodide anion prior to use. In preferred embodiments, a source of persulfate anion is stored in a non-aqueous, water-free environment.

Compositions according to the invention are useful as sanitizers, disinfectants, high level disinfectants or sterilants. In preferred embodiments, the compositions are capable of passing specific regulatory tests required by both the United States Environmental Protection Agency (EPA) and the United States Federal Drug Agency (FDA). This is a very important aspect of this invention since it enables low concentration iodine-based compositions to successfully traverse the gamut of efficacy tests required by United States and European regulatory provisions. These key efficacy tests include the hard surface carrier test for bacteria, mycobactericidal activity and, most surprisingly, the Association of Official Analytical Chemists (AOAC) sporicidal activity tests against vacuum dried spores. The AOAC sporicidal assay is described in Example 4.

Thus, a "disinfectant" is a chemical agent that eliminates a defined scope of pathogenic organisms, but not necessarily all microbial forms (e.g., not bacterial endospores). A "high-level disinfectant" is a germicide that kills all microbial pathogens, except large numbers of bacterial endospores, when used according to labeling. A "sterilant" is a chemical germicide that achieves sterilization, i.e., can destroy all microbial pathogens, including endospores.

The present invention provides compositions which are useful in a broad range of formulations according to the requirements for a particular application. Germicidal formulations of the invention can have various ratios of free molecular iodine and other iodine species such as iodide and triiodide (hereinafter called the "iodine species ratio"). The iodine species ratio can be made to meet the needs of different applications. Generally, a specific iodine species ratio is required for a certain application. For example, a useful ratio for the disinfection of endoscopes is approximately 1/1.

Uses of Compositions of the Invention

In preferred embodiments, the concentrations of the iodide source, the oxidant, and any additives, are selected such that the resulting composition is substantially non-toxic to mammals, and preferably are substantially non-toxic to humans. Accordingly, the non-toxic compositions of the invention can be used either in vitro or in vivo without undesirable toxicity. Thus, in a preferred embodiment, the germicidal composition of the invention can be formulated for external or internal usage in a human. Another use of such a non-toxic composition is as a bowel disinfectant for use prior to surgical procedures. Examples of external uses for the compositions of the invention include hand dips or swabs for disinfection of skin. Similarly, many veterinary applications are possible, including bovine teat dips and the like.

Compositions according to the invention can be used to disinfect hospital and medical equipment, including, for example, endoscopes, scalpels, dental and surgical equipment, dental water lines, bedpans, hemodialysis equipment, heart-lung machines, and the like. The compositions of the invention can also be used to disinfect veterinary equipment and dip poultry eggs. Furthermore, compositions according to the invention can be employed in industrial applications such as the disinfection of bathrooms, and the like. Many other uses will be apparent to the skilled artisan.

Kits

In another aspect, the invention provides a disinfecting kit for generating free molecular iodine. In preferred embodiments, a kit includes a sealable container, a supply of a slow-acting oxidizer composition disposed within the container in a non-reactive condition, and a supply of iodide salt disposed within the container but isolated from the supply of the slow-acting oxidizer. In preferred embodiments, the slow-acting oxidizer is in a non-aqueous state. The slow-acting oxidizer is the persulfate anion.

Kits of the invention can be used to conveniently supply a germicidal composition of the invention. For example, a kit can contain premeasured amounts of an iodide salt, a persulfate salt, and any additives desired. The kit can further include instructions for the reconstitution of the composition of the invention and directions for use of the composition for disinfection.

EXAMPLES

Example 1

To quantitatively understand the effect of pH on iodine hydrolysis, molecular iodine was added into buffered solutions at different pH values and the free molecular iodine concentrations in these solutions were measured at different times. All free molecular iodine values cited in this example and the other examples contained in this patent were determined according to the potentiometric method (W. Gottardi, 1983, *Fresenius Z. Anal Chem.* 314:582–585). The advantage of the potentiometric method is that the concentration of free molecular iodine is determined directly in solution without subsequent manipulations, such as extraction or equilibrium dialysis. This provides a much more accurate measurement.

Table 1 presents the rate of iodine hydrolysis expressed as per cent of free molecular iodine lost. The zero time, value of free molecular iodine is considered to equal 100%. When the pH of a solution was over 7, iodine was hydrolyzed very rapidly. However, iodine hydrolyzes slowly when the pH is 6 or lower. Under the best of circumstances the effect of a rapid rate of hydrolysis is to require more iodide and persulfate which adds to cost and makes the product more bulky. In most cases a rapid rate of hydrolysis eliminates the possibility for an effective product.

TABLE 1

Free % molecular iodine lost via hydrolysis versus pH and time

| Time (h) | pH 3 | pH 4 | pH 5 | pH 6 | pH 7 | pH 8 |
|---|---|---|---|---|---|---|
| 1 | 0.3 | 0 | 0 | 0 | 21.1 | 77.8 |
| 6 | 4.9 | 2.6 | 4.9 | 6.4 | 45.3 | 95.4 |
| 71 | 12.0 | 8.5 | 10.6 | 31.4 | 100 | 100 |

Example 2

The rate of iodine generation that was produced by a combination of sodium persulfate and iodide anions was measured in solutions of different pH. The concentration of free molecular iodine was measured at different pH values as function of time using the potentiometric iodine method of Gottardi. The results of these measurements are presented in Table 2.

TABLE 2

Effect of pH on free molecular iodine concentration (ppm)

| Time (h) | pH 4 | pH 5 | pH 6 | pH 7 | pH 8 | pH 9 |
|---|---|---|---|---|---|---|
| 1 | 11.7 | 13.6 | 11.9 | 13.3 | 9.2 | 3.7 |
| 4 | 51.9 | 54.3 | 46.2 | 50.4 | 34.9 | 11.9 |
| 7 | 105.4 | 105.5 | 99.6 | 97.6 | 64.1 | 15.7 |

A 1.32 molar ratio of sodium iodide (1.0 g/l) over sodium persulfate (1.2 g/l) was used in the experimental formula. The results indicate that free molecular iodine generation is much lower in the solutions at pH values that are greater than 8, while pH has little effect on free molecular iodine when pH is lower than 7. This experiment, together with the results shown in Example 1, show that the most practical pH range for compositions of the invention is pH 3.5 to pH 6.5.

Example 3

A formulation was prepared that started without an initial iodine source. The term "initial iodine" here, as well as the following examples, includes all titrable iodine which is not generated by persulfates. Initial iodine is that thiosulfate titratable iodine either added into system at the beginning or quickly generated by other methods. To a pH 4.5 buffer solution at room temperature, sodium iodide was added to a concentration of 1000 ppm, and then sodium persulfate was dissolved into the system in an amount to make a concentration of 0.1 % (w/v). Any buffer with pH at 4.5 can be used, but a buffer system composed of 20 millimolar citric acid and a base such as sodium citrate and sodium carbonate was used for this example. Loss of iodine from evaporation was prevented by sealing the container. The free molecular iodine in the system gradually increased from zero at the initial time point to over 300 ppm over a period of two days.

Example 4

A formulation was developed using the persulfate-iodine generating system that was suitable for sporocidal assay under AOAC (Association of Official Analytical Chemists) methods. To make a claim as a sterilant or a sporocide with the Federal Drug Administration, a germicide product in the United States must pass the Association of Official Analytical Chemists sporocidal activity test (AOAC sporocidal assay).

To a pH 4.5 solution buffered with sodium citrate and containing 100 ppm initial titrable iodine with 65 ppm as free molecular iodine, sodium persulfate was added to a concentration of 0.07%. The initial iodine can be achieved either by an addition of iodine crystals or by generation with other chemical methods. After addition of sodium persulfate, the disinfection solution was tested according to the AOAC sporocidal method and the composition killed all of the vacuum dried *Bacillus subtilis* spores that were coated on 60 porcelain penicylinders in 18 hours at 30° C. The identical experiment was repeated using *Bacillus subtilis* spores coated onto Dacron sutures at 20° C. No failures were found when testing this solution against *Bacillus subtilis* spores coated on 5 Dacron sutures in 5 days at 20° C.

Example 5

A formulation was prepared that was suitable for endoscope disinfection. A volume of 23 liters of disinfection solution for endoscopes was made with the following components: 60 g citric acid, 78 g sodium citrate, 7 g sodium iodide, 115 mg horseradish peroxidase, 500 mg urea hydrogen peroxide and 14 g sodium persulfate. After mixing the components for 15 minutes, an endoscope was disinfected using a System 83 Plus endoscope cleaning machine made by Custom Ultrasonics (Buckingham, Pa.) at room temperature. A disinfection cycle included 40 minutes of disinfection and 5 minutes of rinse.

The formulation used in this example was reused 8 different times over the course of 8 hours. The concentration of total iodine in this formulation was measured after each disinfection cycle and it maintained a nearly constant titrable iodine level of 50 ppm. The free molecular iodine was also measured after each disinfection cycle. The concentration of free molecular iodine gradually increased from 20 ppm to 30 ppm. The level of evaporation in the System 83 Plus endoscope cleaning machine is substantial because the instrument is open to the environment and provides for a significant degree of agitation and movement of liquids both of which accelerate evaporation.

Example 6

A composition was composed to improve the efficacy of WESCODYNE. WESCODYNE is a commonly used iodophor distributed by Amsco Corporation (Erie, Pa.). WESCODYNE was diluted 50 fold with water. To the diluted solution, sodium persulfate was added in an amount to provide a concentration of 0.1% (w/v). The free molecular iodine increased over a period time of 30 hours. The free molecular iodine increased by 18% over a period of 8 hours and 45% over 24 hours. Without the addition of sodium persulfate the level of free molecular iodine decreased.

Example 7

An experiment was performed to determine the lower level of free molecular iodine that would provide a substantial inactivation of bacteria when the bacteria were present at an elevated concentration.

Table 7 shows the reduction in the number of *Mycoplasma hominis* colony forming units (cfu) after exposure of the organism to various levels of free molecular iodine in a buffer. The exposed organism was diluted serially (10 fold increments) to enumerate the number of surviving organisms which retain the ability to form colonies on solid agar. Table 7 shows a 10 ppm concentration of free molecular iodine imparts a substantial reduction in the number of viable organisms while lower concentrations are substantially less effective.

TABLE 7

Inactivation of mycoplasma versus free molecular iodine concentration.

| | c7 EOumber of Surviving rganisms | | | |
|---|---|---|---|---|
| Dilution plated | Buffer control | 2 ppm $I_2$ | 5 ppm $I_2$ | 10 ppm $I_2$ |
| 1:10 | tntc[1] | ~200 | 20 | 1 |
| 1:100 | tntc[1] | 8 | 0 | 0 |
| 1:1000 | 180 | 0 | 0 | 0 |
| 1:10000 | 7 | 0 | 0 | 0 |
| 1:100000 | 2 | 0 | 0 | 0 |

[1]tntc = too numerous to count

Example 8

An experiment was conducted to demonstrate that it is possible to oxidize a reserve or bank of iodide to form iodine in a controlled gradual fashion. This controlled gradual oxidation of iodide allows one to maintain a constant level of thiosulfate titratable iodine even in the presence of evaporation. In order to ensure the practical applicability of this formulation experiments were conducted to demonstrate the suitability of this composition to disinfect endoscopes in a Custom Ultrasonics System 83 automated endoscope disinfection instrument. The experiment was conducted at 30° C. and an endoscope was disinfected 15 times during the course of this experiment. At defined time points the concentration of thiosulfate titratable iodine and iodide was measured. Iodide was measured using an ion sensitive electrode (Orion Corporation, Cambridge, Mass.).

Five gallons of the iodine germicide was added to the Custom Ultrasonic 83. Each liter of the germicide comprised the following materials: 4.85 grams of citric acid, 2.14 grams of sodium carbonate; 15 milligrams of sodium percarbonate, 500 milligrams of sodium persulfate; 200 milligrams of sodium iodide, and 5 milligrams of horseradish peroxidase. The solution was stirred until it was dissolved, then brought to a temperature of 30° C. and then allowed to incubate for 20 minutes. Measurement were made after the 20 minute incubation (i e., t=0). The measurements of total iodine are shown below in Table 8.

TABLE 8

Total iodine and iodide concentration versus time.

| Time (hrs) | % Initial Iodide | % Initial Total Iodine |
|---|---|---|
| 0 | 100 | 100 |
| 0.5 | 95 | 100 |
| 1 | 91 | 102 |
| 1.5 | 86 | 102 |
| 2 | 85 | 106 |
| 2.5 | 83 | 106 |
| 3 | 79 | 108 |
| 3.5 | 78 | 107 |
| 4 | 77 | 107 |
| 4.5 | 73 | 108 |
| 5 | 70 | 108 |

TABLE 8-continued

Total iodine and iodide concentration versus time.

| Time (hrs) | % Initial Iodide | % Initial Total Iodine |
|---|---|---|
| 5.5 | 70 | 107 |
| 6 | 69 | 106 |
| 6.5 | 66 | 105 |
| 7 | 65 | 103 |
| 7.5 | 64 | 100 |
| 8 | 61 | 100 |
| 8.5 | 60 | 99 |
| 9 | 58 | 99 |

Those skilled in the art will recognize, or be able to ascertain using no more than routine experimentation, numerous equivalents to the specific procedures described herein. Such equivalents are considered to be within the scope of this invention and are covered by the following claims.

Example 9

A composition was dissolved in one liter of water at room temperature and held in a glass jar that was sealed at its top with a screw-top lid. Buffering agents were added to control the pH at 4.5, namely 0.79 grams of sodium carbonate and 19.2 grams of citric acid. A small amount of hydrogen peroxide in the form of sodium percarbonate (0.016 grams) and 1 milligram of peroxidase (Enzyme Commission number 1.11.1.7) were added to provide an initial level of free molecular iodine. Sodium iodide at a concentration of 200 ppm and sodium persulfate at a concentration of 500 ppm were added to provide generation of free molecular iodine for an extended period of time.

TABLE 9

Total iodine concentration versus time.

| Time (hrs.) | Total Iodine | % of Initial Total Iodine |
|---|---|---|
| 0.33 | 24 | — |
| 1 | 25 | 104 |
| 17 | 55 | 229 |
| 24 | 66 | 275 |
| 43 | 84 | 350 |
| 71 | 106 | 442 |
| 137 | 132 | 550 |
| 169 | 138 | 575 |
| 215 | 143 | 596 |
| 312 | 147 | 613 |

This experiment was conducted to demonstrate that it is possible to oxidize a reserve or bank of iodide to form iodine over an extended period of time. The experiment was conducted at room temperature (i.e., 20 to 25° C.) and a composition was formulated to provide continuous oxidation of iodide for at least 13 days. At defined time points the concentration of thiosulfate titratable iodine was measured. Table 9 above shows the concentration of total iodine as a function of time.

Example 10

An experiment was conducted to demonstrate that it is possible to oxidize a reserve or bank of iodide in a controlled gradual fashion and that both (a) the concentration of iodide and persulfate and (b) the ratio of iodide to persulfate effects the rate of oxidation of iodide to free molecular iodine. A series of compositions that had differing concentrations and ratios of iodide and sodium persulfate were formulated. The concentration of total iodine was measured at different time points during the first seven hours of the reactions and the rate of iodine generation in parts per million (ppm) was determined.

The experiment was conducted at room temperature (i.e., 20 to 25° C.) using distilled water that was buffered with citric acid/carbonate at a concentration of 0.010 molar. Each of the persulfate/iodide compositions were dissolved in one liter of buffered water and held in a glass jar that was sealed at its top with a screw-top lid. Table 10 below shows the rate at which iodine is generated as a function of the concentration of iodide and the ratio of persulfate/iodide.

TABLE 10

Rate of iodine generation in parts per million per hour versus (a) concentration of iodide and persulfate and (b) the ration of iodide/persulfate.

| Sodium Iodide Concentration | Ratio of Persulfate to Iodide | | | | |
|---|---|---|---|---|---|
| (mM) | 0.6 | 1.3 | 1.75 | 2 | 3 |
| 0.6 | — | 0.2 | 0.4 | 0.5 | 0.5 |
| 1.2 | 0.6 | 1.2 | 1.8 | 2.1 | 2.9 |
| 1.8 | 1.4 | 3.8 | 4.2 | 5.2 | 7.4 |
| 2.4 | 2.9 | 6.8 | 8.8 | 9.8 | 13.1 |

The data shows that within each of the formulation series that have a constant iodide to persulfate ratio, the rate of iodine generation increases as the concentration of sodium iodide is increased. At a fixed concentration of iodide, the rate of iodine generation increases as the ratio of persulfate/iodide is increased. The principal means to control the rate of oxidation of iodide anion by the peroxydisulfate anion is the vary the concentration of either or both of these species. It is clear that it is possible to control the rate of iodine generation across a broad range by varying wither or both of these species.

Example 11

A series of compositions that had differing concentrations and ratios of iodide and sodium persulfate were formulated. Each of the persulfate/iodide compositions were dissolved in one liter of water buffered to a pH of 5.0 with 50 mM sodium citrate. The activated formulations were held at room temperature in glass jars that were sealed via a screw-top lid. The formulations contained various concentrations of persulfate anion and iodide anion such that both (a) the concentration of iodide and persulfate were varied and (b) the ratio of iodide to persulfate were varied to the concentration extremes identified in this application. The concentration of total iodine was measured at different time points during the course of this reaction.

Table 11 below identifies the concentration of iodide and persulfate and the time required to oxidize 10% of the initial iodine anion, identified as the $T_{10}$ value in Table 11. Experiments 3 and 4 identify conditions wherein a high concentration of iodine is rapidly formed. Experiment 1 identifies conditions wherein it takes more than 24 hours to achieve a 5 ppm iodine concentration. This type of formulation is useful for situations where it is necessary to disinfect and preserve sensitive materials over the course of several days such as the disinfection of dialysis instrumentation over a weekend. It is clear from Table 11 that the generation of iodine is a function of both the persulfate anion and iodide anion.

TABLE 11

Time required to oxidize 10% of the initial iodide anion in parts per million versus the concentration of iodide and persulfate.

| | Experiment # | | | |
|---|---|---|---|---|
| Concentration (ppm) | 1 | 2 | 3 | 4 |
| Iodide anion | 50 | 50 | 10,000 | 10,000 |
| persulfate anion | 100 | 10,000 | 100 | 10,000 |
| $T_{10}$ | 1530 | 13 | 11 | 8 |

Table 11a below shows the total iodine concentration versus time for the identical four compositions used in the experiment described in Table 11. The data in Table 11a shows the total iodine concentration as a function of time for a period of seventy hours.

TABLE 11a

Titratable iodine in part per million (ppm) versus time.

| Time (min) | Experiment 1 | Experiment 2 | Experiment 3 | Experiment 4 |
|---|---|---|---|---|
| 10 | | 3.8 | 11.4 | 1129 |
| 20 | | 8.2 | 22.2 | 2161 |
| 40 | | 165 | 40.6 | 3502 |
| 60 | | 24.1 | 59 | 4663 |
| 120 | | 34.3 | 87.6 | 5869 |
| 180 | | 41.9 | 106 | ppt |
| 240 | | 46.3 | 118 | |
| 4200 | 14 | 47 | 125.6 | |

The data is Table 11a demonstrate that a wide range of compositions with diverse properties can be generated using the conditions described in this application. For instance, Experiment 1 shows that it is possible to provide a sustained low level of iodine generation for a prolonger time period. Experiment 4 demonstrates that iodine can be generated at such a rapid rate that iodine precipitation can occur. This underscores the fact that a preferred composition of matter can only be formulated once the conditions of use are fully understood. For instance, if the formulation used in Experiment 4 was placed under conditions such that 75 ppm per minute of free molecular iodine were evaporating, then precipitaiton would not occur during the timeframe of this experiment.

The contents of all references and patent applications described herein are hereby incorporated by reference.

Other embodiments are within the scope of the following claims.

What is claimed is:

1. A method of preparing a disinfecting iodine solution in which free molecular iodine is generated at a controlled average rate of at least 0.2 ppm per hour over a sustained time period comprising the steps of:

combining a persulfate anion having an initial minimum concentration of at least 100 ppm and an iodide anion having an initial minimum concentration of at least 50 ppm in an aqueous medium having a resulting pH of less than about 6.5 to cause the iodide to oxidize slowly and to form an iodide bank of excess iodide ions such that free molecular iodine is generated at a concentration of at least 5 ppm and at a controlled iodine generating capacity of between 1.5 and 36 with the iodide bank of excess iodide ions having an iodide concentration at least equal to the concentration at which the free molecular iodine is generated and with the generated level of free molecular iodine being sustained above said minimum concentration over a controlled time period until the iodide bank is essentially exhausted.

2. The method of claim 1 wherein the minimum ratio of said iodine anion to said persulfate anion is ½.

3. The method of claim 2 wherein the minimum ratio of said iodide anion to said persulfate anion is ½ such that a concentration of 5 ppm of free molecular iodine is generated in said solution and sustained in said solution for a defined time period.

4. The method of claim 3 wherein the persulfate anion is generated from a persulfate salt selected from the group consisting of sodium persulfate, ammonium persulfate and potassium persulfate.

5. The method of claim 4 wherein the iodide anion if generated from an iodide salt selected from the group consisting of potassium iodide and sodium iodide or other simple salts of iodide.

6. The method of claim 5 wherein said sustained time period is equal to at least 1 hour and up to a maximum of 30 days.

7. The method of claim 1 further comprising the step of adding a source of iodine independent of said iodide anion to said aqueous medium to establish an initial iodine concentration of at least 10 ppm.

8. The method of claim 7 wherein said iodine source is selected from the group consisting of elemental iodine, iodophor and a mixture thereof.

9. A disinfecting iodine composition which will cause a sustained release of free molecular iodine for an extended time period at a minimum concentration of 5 ppm when added to an aqueous medium comprising:

a persulfate anion in a minimum initial concentration of 100 ppm;

an iodide anion in a minimum initial concentration of 50 ppm; and a buffering agent to reduce the resulting pH of said aqueous medium to less than about 6.5 such that an iodide bank is formed in said aqueous medium having a reserve of iodide ions in a concentration at least equal to the concentration at which the free molecular iodine is generated whereby the Generation of free molecular iodine is sustained above said minimum concentration over the course of said time period and until the iodide bank is essentially exhausted.

10. A disinfecting iodine composition as claimed in claim 9 wherein the ratio of said iodide anion to said persulfate anion is from 1/200 to 100/1 for controlling the iodine generating capacity and rate of generating free molecular iodine is said aqueous medium.

11. A disinfecting iodine composition as claimed in claim 10 wherein said persulfate salt is selected from the group consisting of sodium persulfate, ammonium persulfate, potassium persulfate and other simples salts of persulfate known to be converted into peroxydisulfate anion in solution.

12. A disinfecting iodine composition as claimed in claim 11 wherein said iodide salt is selected from the group consisting of sodium iodide, potassium iodide and other simple salts of iodide known to be converted into iodide anion in solution.

13. A disinfecting iodine composition as claimed in claim 9 wherein said extended time period is equal to at least one hour and up to a maximum of 30 days.

14. A disinfecting iodine composition as claimed in claim 13 further comprising a source of iodine independent of said iodide anion for establishing an initial iodine concentration in said iodine composition.

15. A disinfecting iodine composition as claimed in claim 14 wherein said iodine source is selected from the group consisting of elemental iodine, iodophore, a quick oxidant and a mixture thereof.

* * * * *